United States Patent [19]

Smith et al.

[11] Patent Number: 4,529,588

[45] Date of Patent: Jul. 16, 1985

[54] HAIR CONDITIONING SHAMPOO

[75] Inventors: Walter P. Smith, Scuddy Hook; Lori J. Dunn, Stamford, both of Conn.

[73] Assignee: Richardson-Vicks Inc., Wilton, Conn.

[21] Appl. No.: 584,012

[22] Filed: Feb. 27, 1984

[51] Int. Cl.$^3$ .............. A61K 7/06; A61K 7/08
[52] U.S. Cl. .............. 424/70; 424/DIG. 4
[58] Field of Search .............. 424/70

[56] References Cited

U.S. PATENT DOCUMENTS

| | | | |
|---|---|---|---|
| 3,766,267 | 10/1973 | Zak et al. | 424/320 |
| 3,855,290 | 12/1974 | Zak et al. | 424/70 |
| 4,075,131 | 2/1978 | Sterling | 424/78 X |
| 4,110,263 | 8/1978 | Lindemann et al. | 424/70 |
| 4,247,538 | 1/1981 | Barker | 424/70 |
| 4,438,096 | 3/1984 | Preston | 424/70 |

FOREIGN PATENT DOCUMENTS 120800  9/1981  Japan .............. 424/70

*Primary Examiner*—Dale R. Ore
*Attorney, Agent, or Firm*—Salvatore R. Conte

[57] ABSTRACT

An improved aqueous hair conditioning shampoo composition containing about 0.5–10 percent by weight of cocamidopropyl hydroxysultaine and about 0.1–6 percent by weight of a quaternary halide of an N,N,N-trialkylaminoalkylene gluconamide, the improvement being the inclusion of about 5–20 percent by weight of a mixture of two surfactants, ammonium lauryl sulfate and triethanolamine lauryl sulfate, in a 1:1 to 5:1 ratio, respectively.

5 Claims, No Drawings

HAIR CONDITIONING SHAMPOO

FIELD OF THE INVENTION

This invention relates to improved cosmetics for use in hair treatment and, more particularly, to enhancing the cosmetic properties of hair conditioning shampoos which contain two essential ingredients, cocamidopropyl hydroxysultaine and certain quaternary halides of N,N,N,-trialkylaminoalkylene gluconamide, by the inclusion of two surfactants, ammonium lauryl sulfate and triethanolamine lauryl sulfate.

BACKGROUND OF THE INVENTION

One of the essential ingredients in the subject hair conditioning shampoo composition is cocamidopropyl hydroxysultaine, also known chemically as 3-[(3-cocamidopropyl)dimethylammonio]-2-hydroxypropanesulfonate. Cocamidopropyl hydroxysultaine is the adopted name of the Cosmetic, Toiletry and Fragrance Association (CFTA) for the zwitterion (inner salt) conforming to the formula:

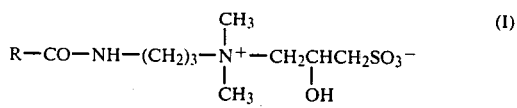

wherein R—CO— represents the coconut acid radical. It is an amphoteric surfactant recommended for use in cosmetics and toiletries including, among others, as a base in hair conditioning shampoos. The sultaine is commercially available in the form of a free-flowing 50% aqueous solution (i.e., 50% actives) under such names as "Lonzaine® CS" and "Mirataine® CBS". As noted, its use in hair conditioning shampoos is known. For example, in the April 1980 product information bulletin supplied by Lonza Inc. of Fair Lawn, N.J. on its trademark brand of cocamidopropyl hydroxysultaine, "Lonzaine CS", the specific use of this component in conditioning shampoos is described and exemplified. Similar application in conditioning shampoos is also described and exemplified by the Miranol Chemical Company, Inc. of Irvington, N.J. in the product information bulletin on its trademark brand of cocamidopropyl hydroxysultaine, "Mirataine CBS".

The second essential ingredient in the subject hair conditioning shampoo composition is a quaternary halide of an N,N,N-trialkylaminoalkylene gluconamide having the formula:

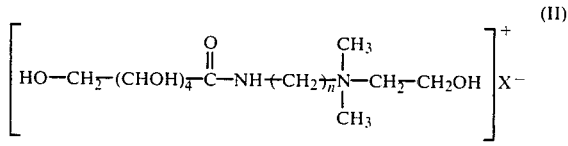

wherein X is chloro or bromo and n is an integer of from 2 to 4, and preferably 3, of which the quaternary chloride salt having the following formula is most preferred:

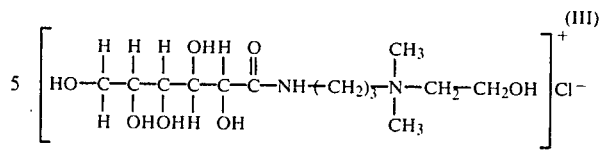

Said quaternary halide salts are described in U.S. Pat. Nos. 3,766,267 and 3,855,290 for use as emollients in topical and cosmetic applications. The preferred quarternary chloride salt of formula (III), chemically known as α-gluconamidopropyl dimethyl-2-hydroxyethyl ammonium chloride (CTFA name: Quaternium 22), is commercially available as a free-flowing 60% aqueous solution (i.e., 60% actives) marketed by the Van Dyk Company, Inc. of Belleville, N.J., under the trademark "Ceraphyl 60".

In now abandoned U.S. patent application Ser. No. 433,565, which application is incorporated herein by reference, entitled "Improved Hair Conditioning Shampoo", filed Oct. 4, 1982 by, among others, Walter P. Smith, one of the co-inventors of the instant application, and in issued South African Pat. No. 83/7075 claiming priority of said Ser. No. 433,565, the combined use of the aforementioned cocamidopropyl hydroxysultaine (I) and quaternary halide (II) components in an aqueous hair conditioning shampoo composition was disclosed and claimed. It was shown therein that such compositions provide for an increased deposition of said conditioning components on the surface of hair shampooed therewith and, moreover, it does so without a concomitant substantial loss of activity in reducing the spreadability of sebum.

Sebum, or "skin oil" is produced by the sebaceous glands of the skin, including the scalp, and it migrates to the hair by capillary action. After shampooing, the surface of the hair is devoid of sebum. The hair surface becomes "oily" as sebum migrates along the hair shaft. By reducing or slowing down sebum migration, for example, by adding materials providing such action to the shampoo which are deposited on the hair surface after rinsing, the hair surface stays less oily for a longer period. Said quaternary halide salts of formula (II), and preferably of formula (III) were found to provide such action in aqueous hair conditioning shampoos containing the aforementioned cocamidopropyl hydroxysultiane (I), as shown in the aforementioned now abandoned U.S. patent application Ser. No. 433,565 and said South African Pat. No. 83/7075. The aqueous hair conditioning shampoo compositions disclosed and claimed therein contain about 0.5–10 weight percent (0.5–5 percent preferred) of component (I) and about 0.1–6 weight percent (0.6–3 percent preferred) of component (II) with best results obtained at about pH 3–6.8 (pH 5.5–6.8 preferred).

The present invention resides in improved compositions useful for shampooing and conditioning hair, preferably oily hair, and constitutes an improvement of the aforementioned aqueous hair conditioning shampoo compositions of said now abandoned Ser. No. 433,565 and said South African Pat. No. 83/7075, the improvement being the inclusion in such conditioning shampoos of two specific surfactants, ammonium lauryl sulfate and triethanolamine lauryl sulfate in specified amounts and ratios.

DETAILED DESCRIPTION OF THE INVENTION

It has now been found that aqueous hair conditioning shampoo compositions containing from about 0.5 to about 10 percent, and preferably from about 0.5 to about 5 percent, by weight of the amphoteric surfactant, cocamidopropyl hydroxy sultaine (I) and from about 0.1 to about 6 percent, and preferably from about 0.6 to about 3 percent, by weight of the N,N,N-trialkylaminoalkylene gluconamide halide salt of formula (II), are improved by utilizing, as the sole anionic and primary surfactant component in said compositions, from about 5 to about 20 percent, and preferably from about 5 to about 15 percent, by weight of a combination of two specific anionic surfactants, ammonium lauryl sulfate (ALS) and triethanolamine lauryl sulfate (TEALS) in a respective weight ratio of from about 1:1 to about 5:1 and preferably from about 2:1 to about 4:1.

The subject compositions are particularly suited for use with oily hair due to the marked reduction in sebum spreading afforded by said ALS/TEALS combination. Such sebum spreading reduction, that is, control of sebum regreasing or sebum migration, is enhanced by about 30-60% over the same shampoo composition containing an equal amount of either ALS or TEALS alone as the primary surfactant. The superior controlling ability of said ALS/TEALS combination is also evident over the other anionic primary surfactants conventionally used in shampoos such as, for example, sodium lauryl sulfate (SLS), sodium lauryl sarcosinate, sodium lauryl ether sulfate (SLES) and the like. The primary surfactant in shampoo formulations is commonly recognized as the main cleansing and foaming agent for doing the basic shampooing job, namely, to clean the hair of scalp oils, dirt and bacteria.

The marked improvement in the rate of sebum regreasing obtained with the compositions of the invention will be readily evident from the recorded test data in the following tables. The data also reveal the absence of any effect on the amount of conditioner deposition of components (I) and (II) resulting from the combined use of ALS and TEALS.

The procedure utilized in testing for the rate of sebum migration is described in Int. J. of Cos. Sci., Vol. 1, p. 169-176 (1979) as modified hereinafter. The test methodology involves human hair bundles (approximately ten virgin hairs per bundle; the hairs are commercially available from De Meo Bros., New York, N.Y.) which are defatted with hexane, treated with the composition to be tested as described and then air-dried and fastened in a vertical orientation in a sebum migration chamber as described. A measured portion of the bottom of the hair bundle is placed into a reservoir of artificial sebum and sebum is allowed to migrate up the hair shafts for 30 minutes, after which time the hair bundle is removed from the reservoir and transferred on to a silica gel plate (Siliga Gel G, Analtech Inc., Newark, Del.) by pressing the hair bundle against the plate with tissue paper. The plate is sprayed with a 50-50 solution of concentrated sulfuric acid and water and then heated at 220° C. for 15 minutes. The resultant brown tracks which develop on the plate correspond to the distances over which the sebum migrates along the hair bundles. These tracks are measured and the sebum migration is expressed as centimeters migrated per hour (i.e., the rate of sebum regreasing). All values are "normalized" with respect to a non-treated hair bundle as the control by dividing the rate obtained from a treated hair bundle by the rate obtained from the non-treated control. Thus, the "normalized rate of sebum regreasing" is expressed as a dimensionless number, a number less than 1.0 indicating a reduced rate of sebum regreasing and the smaller the number, the greater the reduction in regreasing.

The procedure utilized in testing for deposition of conditioner components is as follows:

Materials Required:
1. 5% Rubine's Dye (Pyrazol Fast Bordeaux) in water, pH 3.5 (adjusted with HCl).
2. 0.1N NaOH in 1:1 w/w abs. EtOH:water.

Protocol:

From 2 to 4 mg/cm$^2$ of the material to be tested is gently rubbed on to the volar forearm for 1 minute and then rinsed with cool tap water for 15 seconds and allowed to air dry. After drying, a 2 cm diameter glass cylinder is placed on the treated site and 1 ml of Rubine's Dye is pipetted into the cylinder. After 1 minute, the cylinder and dye are removed and the arm is rinsed under cool tap water for 15 seconds. The remaining dye on the arm is extracted by placing the glass cylinder at the same site and adding 1 ml of the 0.1 N NaOH ethanolic solution. The extraction step, which is assisted by rubbing with a teflon rod ("policeman") for 1 minute, is repeated. The combined 2×1 ml extractions are diluted to 3.5 ml with the 0.1N NaOH ethanolic solution and read at 520 nm in a colorimeter (e.g., Bausch & Lomb, Spectronic 20 model). The reading obtained is the absorbance of the sample, using a 1 cm path length cuvette. Increased absorbance evidences increased binding of dye to the skin. Since the dye binds to the cationic conditioners at a fixed ratio, an increase in absorbance reflects a corresponding increase in the amount of conditioner deposited, which amount can be readily determined.

For testing purposes herein, aqueous hair conditioning shampoo compositions were prepared containing the indicated amount of hair conditioning components (I) and (II) in combination with the indicated amount of the particular surfactant, methyl and propyl parabens as preservatives (0.5% w/w each) and dilute sodium hydroxide for adjusting the pH to about 6.

In Table 1, the observed normalized rates of sebum regreasing obtained from several such shampoos are listed wherein the amount of surfactant was maintained constant at 14% w/w and the amount of conditioning components (I) and (II) was varied.

TABLE 1

| 14% w/w Surfactant | % w/w Ceraphyl 60 & Mirataine CBS | Conditioner Deposition[1] | Normalized Rate of Sebum Regreasing |
|---|---|---|---|
| TEALS | 1% & 4% | | 0.78 |
| SLES | 1% & 4% | 11 | 0.66 |
| ALS | 1% & 4% | | 0.61 |
| ALS/TEALS (3:1) | 1% & 4% | | 0.40 |
| TEALS | 1% & 7% | | — |
| SLES | 1% & 7% | | 0.73 |
| ALS | 1% & 7% | | 0.59 |
| ALS/TEALS (3:1) | 1% & 7% | | 0.41 |
| TEALS | 1% & 10% | 7 | 0.79 |
| SLES | 1% & 10% | 11 | 0.80 |
| ALS | 1% & 10% | 10 | 0.63 |
| ALS/TEALS (3:1) | 1% & 10% | 12 | 0.39 |
| TEALS | 2% & 4% | | 0.78 |
| SLES | 2% & 4% | | 0.79 |
| ALS | 2% & 4% | | 0.71 |
| ALS/TEALS (3:1) | 2% & 4% | | 0.42 |
| TEALS | 2% & 7% | 8 | 0.93 |
| SLES | 2% & 7% | 9 | 0.81 |

TABLE 1-continued

| 14% w/w Surfactant | % w/w Ceraphyl 60 & Mirataine CBS | Conditioner Deposition[1] | Normalized Rate of Sebum Regreasing |
|---|---|---|---|
| ALS | 2% & 7% | 10 | 0.73 |
| ALS/TEALS (3:1) | 2% & 7% | 12 | 0.41 |
| TEALS | 2% & 10% |  | 0.83 |
| SLES | 2% & 10% |  | 0.67 |
| ALS | 2% & 10% |  | 0.68 |
| ALS/TEALS (3:1) | 2% & 10% |  | 0.42 |

[1] Absorbance at 520 nm × 10⁻²

In Table 2, the observed normalized rate of sebum regreasing obtained from several of the aforementioned shampoo compositions are listed wherein the amount of conditioning components (I) and (II) was maintained constant and varying ratios of the ALS/TEALS surfactant were employed.

TABLE 2

| 14% w/w Surfactant | % w/w Ceraphyl 60 & Mirataine CBS | Conditioner Deposition[1] | Normalized Rate of Sebum Regreasing |
|---|---|---|---|
| TEALS | 2% & 10% |  | 0.83 |
| SLES | 2% & 10% | 12 | 0.67 |
| ALS | 2% & 10% | 15 | 0.68 |
| ALS/TEALS |  |  |  |
| (2:1) | 2% & 10% |  | 0.45 |
| (3:1) | 2% & 10% | 16 | 0.44 |
| (4:1) | 2% & 10% |  | 0.45 |
| (5:1) | 2% & 10% |  | 0.58 |

[1] Absorbance at 520 nm × 10⁻²

In Table 3, the observed normalized rate of sebum regreasing obtained from several of the aforementioned shampoo compositions are listed wherein the amount of conditioning components (I) and (II) was maintained constant and varying amounts of total surfactant were employed.

TABLE 3

| % w/w 3:1 ALS/TEALS | % w/w Ceraphyl 60 & Mirataine CBS | Conditioner Deposition[1] | Normalized Rate of Sebum Regreasing |
|---|---|---|---|
| 6% | 1% & 4% | 18 | 0.39 |
| 14% | 1% & 4% | 16 | 0.44 |
| 20% | 1% & 4% | 15 | 0.44 |

[1] Absorbance at 520 nm × 10⁻²

From the foregoing data, it is evident that hair conditioning shampoo compositions containing cocamidopropyl hydroxysultaine (I) and an N,N,N-trialkylaminoalkylene gluconamide quaternary halide (II), preferably the chloride (III), are unexpectedly and surprisingly improved when the specified amount and relative ratio of the two anionic surfactants, ammonium lauryl sulfate and triethanolamine lauryl sulfate, are utilized as the sole anionic and primary surfactant component in said compositions. For example, a comparison of the normalized rates of sebum regreasing observed in Table 2 for the 2:1 to 4:1 ratio of ALS/TEALS (14% w/w) surfactant constitutes about a 35% improvement over that observed for the same amount of ALS alone or SLES alone and about a 47% improvement over the same amount of TEALS alone.

Any conventional aqueous hair shampoo formulation can be used as the shampoo base of the subject compositions. Such formulations are well known in the art and are not discussed in detail herein. The particular type of hair conditioning shampoo composition, which may include gels, creams, lotions, solutions, emulsions and the like just to name a few, is not critical. Such types of compositions are readily prepared by skilled cosmetic chemical formulators. The components (I) and (II) are non-toxic to human skin, are compatible with hydrophilic adjuvants and can be readily incorporated into such compositions. Although said components are utilizable over a wide pH range, best results for purposes of this invention are found when used in acidic hair conditioning shampoos, for example, from about pH 3 to about 6.8 and, preferably from about pH 5.5 to about 6.8.

It will be understood by those having skill in the art that the invention is not limited to the specific examples which have been offered as particular embodiments and that modifications can be made without departing from the spirit thereof.

We claim:

1. In an improved aqueous hair conditioning shampoo composition containing, percentages given being by weight based upon the total weight of the composition, from about 0.5 to about 10 percent of cocamidopropyl hydroxysultaine and from about 0.1 to about 6 percent of a quaternary halide of an N,N,N-trialkylaminoalkylene gluconamide having the formula:

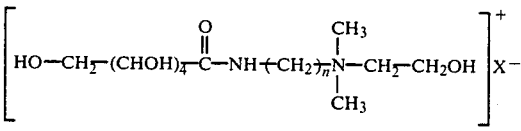

wherein X is chloro or bromo and n is an integer of from 2 to 4, the improvement which comprises including, as the sole anionic and primary surfactant component of said composition, from about 5 to about 20 percent of combined ammonium lauryl sulfate and triethanolamine lauryl sulfate in a respective weight ratio of from about 1:1 to about 5:1.

2. In an improved aqueous hair conditioning shampoo composition containing, percentages given being by weight based upon the total weight of the composition, from about 0.5 to about 10 percent of cocamidopropyl hydroxysultaine and from about 0.1 to about 6 percent of a quaternary chloride of an N,N,N-trialkylaminoalkylene glyconamide having the formula:

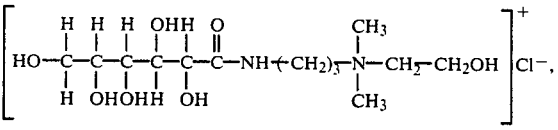

the improvement which comprises including, as the sole anionic and primary surfactant component of said composition, from about 5 to about 20 percent of combined ammonium lauryl sulfate and triethanolamine lauryl sulfate in a respective weight ratio of from about 1:1 to about 5:1.

3. The improved composition of claim 2 wherein said weight ratio is from about 2:1 to about 4:1.

4. An improved aqueous hair conditioning shampoo composition containing, percentages given being by weight based upon the total weight of the composition, from about 0.5 to about 5 percent of cocamidopropyl hydroxysultaine and from about 0.6 to about 3 percent of a quaternary chloride of an N,N,N-trialkylaminoalkylene gluconamide having the formula:

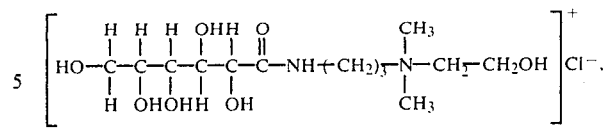

the improvement which comprises including, as the sole anionic and primary surfactant component of said composition, from about 5 to about 15 percent of combined ammonium lauryl sulfate and triethanolamine lauryl sulfate in a respective weight ratio of from about 1:1 to about 5:1.

5. The improved composition of claim 4 wherein said weight ratio is from about 2:1 to about 4:1.

* * * * *